(12) United States Patent
Zeng et al.

(10) Patent No.: US 12,099,052 B2
(45) Date of Patent: Sep. 24, 2024

(54) METHOD FOR DETECTING HUMAN INGESTED SUBSTANCE AND INGESTION TIMES

(71) Applicant: XIAMEN LISI TECH SERVICE CO., LTD., Xiamen (CN)

(72) Inventors: Zhiyin Zeng, Xiamen (CN); Kongtao Zhu, Xiamen (CN); Hui Wu, Xiamen (CN); Jiansheng Zeng, Xiamen (CN)

(73) Assignee: XIAMEN LISI TECH SERVICE CO., LTD., Xiamen (CN)

( * ) Notice: Subject to any disclaimer, the term of this patent is extended or adjusted under 35 U.S.C. 154(b) by 1106 days.

(21) Appl. No.: 16/805,776

(22) Filed: Mar. 1, 2020

(65) Prior Publication Data

US 2021/0156845 A1   May 27, 2021

(51) Int. Cl.
*G01N 33/50*   (2006.01)
*A61B 5/00*   (2006.01)
*H01J 49/40*   (2006.01)

(52) U.S. Cl.
CPC ....... *G01N 33/5038* (2013.01); *A61B 5/4833* (2013.01); *H01J 49/40* (2013.01)

(58) Field of Classification Search
CPC .... G01N 33/5038; A61B 5/4833; H01J 49/40
See application file for complete search history.

(56) References Cited

PUBLICATIONS

Miki, Akihiro, et al. "MALDI-TOF and MALDI-FTICR imaging mass spectrometry of methamphetamine incorporated into hair." Journal of Mass Spectrometry 46.4 (2011): 411-416. (Year: 2011).*

* cited by examiner

*Primary Examiner* — Robert J Eom

(57) ABSTRACT

A method for detecting ingestion times comprises the following steps: obtaining hair samples or nail samples; sampling hair samples or nail samples per unit length, and judging whether the target ingested substance and its metabolites are present in each sample; and counting times of detected target ingested substance and its metabolites as the ingestion times.

7 Claims, 6 Drawing Sheets

S1, acquiring the mass spectrum in the terminal of each matrix assisted laser ionization analysis time-of-flight mass spectrometer, and storing each mass spectrum and its corresponding identity information, sampling time and residence information when sampling in the database;

S2, obtaining the mass spectrum characteristic ion peaks of known substances and / or unknown substances in each mass spectrum S3, counting the frequency of the mass spectrum characteristic ion peak of the known substance and / or the unknown substance, and early warning of the mass spectrum characteristic ion peak whose frequency is greater than the first threshold S1, acquiring the mass spectrum in the terminal of each matrix assisted laser ionization analysis time-of-flight mass spectrometer, and storing each mass spectrum and its corresponding identity information, sampling time and residence information when sampling in the database;

S2, obtaining the mass spectrum characteristic ion peaks of known substances and / or unknown substances in each mass spectrum S3, counting the frequency of the mass spectrum characteristic ion peak of the known substance and / or the unknown substance, and early warning of the mass spectrum characteristic ion peak whose frequency is greater than the first threshold

FIG.1

METHOD FOR DETECTING HUMAN INGESTED SUBSTANCE AND INGESTION TIMES

CROSS REFERENCE TO RELATED APPLICATIONS

This application claims all benefits accruing under 35 U.S.C. § 119 from China Patent Application No. 201911174923.8, filed on Nov. 26, 2019, in the China National Intellectual Property Administration, the disclosure of which is incorporated herein by reference.

TECHNICAL FIELD

The present invention generally relates to detecting human ingested substance, and more particularly to a method for detecting human ingested substance and ingestion times.

BACKGROUND

At present, the number of cases involving drugs, stimulants or psychotropic substances is on the rise, so the in vivo analysis of drugs, stimulants or psychotropic substances and their metabolites has attracted more and more attention. At present, body fluid is still the most commonly used biological test samples for drug abuse. However, the detection time of drugs, stimulants or psychotropic substances in body fluid is short, and the samples are not easy to preserve. However, the hair is easy to take, easy to carry, easy to store for a long time, and the metabolism of drugs in the hair is slow and can exist for a long time. The hair segmentation analysis can infer the history of drugs, stimulants or psychotropic substances. Therefore, the hair analysis has irreplaceable advantages in the identification of drug abuse. But at present, the identification of hair generally needs complex processes such as grinding, hydrolysis, extraction, chromatography. In addition, in the prior art, it is impossible to detect the ingestion times of drug, stimulant or psychotropic drugs.

SUMMARY OF THE DISCLOSURE

The disclosure provides a method for detecting human ingested substance and ingestion times, which can effectively solve the above problems.

The disclosure is realized as follows:

A new method for detecting human ingested substance comprises the following steps:

S1, obtaining biological test samples;

S2, fixing the biological test sample added with a matrix solution on a target plate;

S3, acquiring spectrum of biological test samples added with a matrix solution with a matrix assisted laser ionization time-of-flight mass spectrometer, and taking whether the spectrum of a target ingested substance and its metabolites have the characteristic ion peak of mass spectrum as the basis of whether the target ingested substance is ingested.

The disclosure further provides a new method for detecting ingestion times of human ingested substance, which comprises the following steps:

S1, obtaining hair samples or nail samples;

S2, fixing the hair samples or nail samples added with a matrix solution on a target plate;

S3, acquiring spectrum of hair samples or nail samples added with a matrix solution per unit length with a matrix assisted laser ionization analysis time-of-flight mass spectrometer, and taking whether the spectrum of the target ingested substance and its metabolites have the characteristic ion peak of mass spectrum as the basis of whether the target ingested substance is ingested;

S4, counting times of target ingested substance and its metabolites as the ingestion times.

The disclosure further provides a new method for detecting ingestion times of human ingested substance, comprising the following steps:

S1, obtaining hair samples or nail samples;

S2, sampling hair or nail samples per unit length and judging whether the target ingested substance and its metabolites are present in each sample;

S3, counting times of target ingested substance and its metabolites as the ingestion times.

The hair samples or nail samples are processed and added with a matrix solution. The spectrums of the hair and nail samples are acquired by a matrix assisted laser ionization analysis time-of-flight mass spectrometer, so that the hair samples or nail samples can be quickly tested for human ingested substances (especially drugs, stimulants and psychotropic substances), so as to avoid complex grinding, hydrolysis, extraction and other processes. In addition, through the selection of the matrix solution and laser power, the disclosure can effectively and rapidly release the human ingested substance and improve the detection accuracy. Finally, the total number of times of drug use can be obtained by preliminary spectrum acquiring of hair samples or nail samples per unit length, and statistical analysis of the times of spectrum of the mass spectrum characteristic ion peak of human ingested substances in the mass spectrum.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

FIG. 1 is a flow chart of the new method for detecting human ingested substance provided by an embodiment of the disclosure.

DETAILED DESCRIPTION

The disclosure is illustrated by way of example and not by way of limitation in the figures of the accompanying drawings in which like references indicate similar elements. It should be noted that references to "an" or "a" embodiment in this disclosure are not necessarily to the same embodiment, and such references mean "at least one."

Referring to FIG. 1, the embodiment of the disclosure provides a new method for detecting human ingested substance, comprising the following steps:

S1, obtaining biological test samples;

S2, fixing the biological test samples added with a matrix solution on a target plate;

S3, acquiring spectrum of biological test samples added with a matrix solution with a matrix assisted laser ionization analysis time-of-flight mass spectrometer, and taking whether the spectrum of the target ingested substance and its metabolites have the characteristic ion peak of mass spectrum as the basis of whether the target ingested substance is ingested.

In step S1, the biological test samples are preferably hair samples or nail samples, wherein the hair samples are obtained by cutting the hair close to the skin, and the nail samples are obtained by scraping a continuous layer from the root of the nail to the front edge of the nail. The biological test samples can also be blood, saliva or other excreta, etc. In this embodiment, the hair at the occipital part is selected. There is no limit to the number of hair samples and nail samples, preferably 2-3.

In step S1, after obtaining hair samples or nail samples, further comprising:

S1.1 washing the hair samples or the nail samples to remove contaminants.

In step S2, the step of fixing the hair samples or nail samples added with a matrix solution on a target plate comprises:

S2.1, fixing the hair samples or nail samples on a target plate;

S2.2, adding a matrix solution to the hair samples or the nail samples, and volatilizing the solvent.

As a further improvement, the matrix molecules must have strong absorption at the laser wavelength. The matrix in the matrix solution can be one or more of α-cyano-4-hydroxycinnamic acid, 3,5-dimethoxy-4-hydroxycinnamic acid, trihydroxyacetophenone, 3-hydroxypyridylic acid, α-cyano-4-hydroxycinnamic acid, trihydroxyacetophenone, trans-3-indoleacrylic acid, desanthrol and 2,5-dihydroxybenzoic acid. The matrix solution can be formed by dissolving the matrix in a solvent.

As a further improvement, the matrix solution can further comprise an internal standard. The internal standard can be methoxyphenamine, etc.

Figure 2:
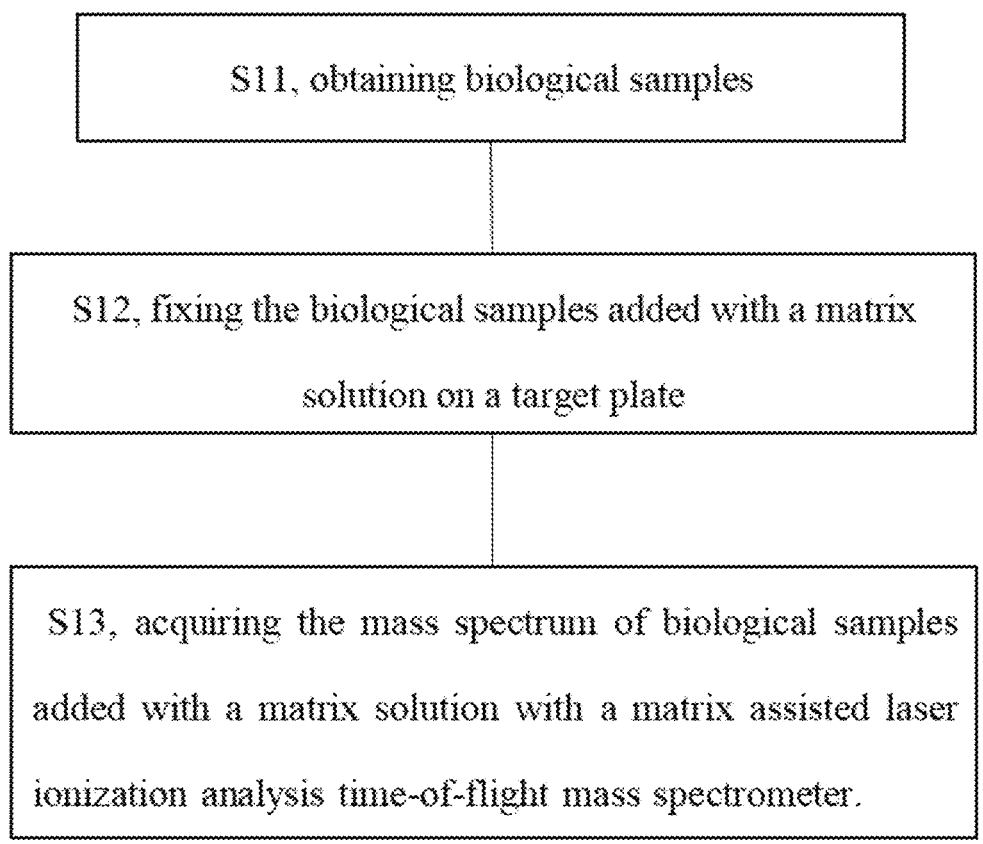
FIG. 2 is a schematic diagram of the detection principle of the matrix assisted laser ionization analysis time-of-flight mass spectrometer according to embodiment 1.

Referring to FIG. 2, in step S3, the step of acquiring spectrum of the hair samples or nail samples added with a matrix solution with a matrix assisted laser ionization analysis time-of-flight mass spectrometer comprises:

S3.1, preliminarily acquiring spectrum of the hair samples or nail samples added with a matrix solution with a matrix assisted laser ionization analysis time-of-flight mass spectrometer per unit length;

The unit length can be selected according to the daily growth rate of human hair. Generally speaking, human hair varies from person to person, with a daily growth rate of about 0.2-0.4 mm. Therefore, preferably, the unit length is also 0.2-0.4 mm.

When the matrix solution further comprises an internal standard, after step S31, it may further comprise:

S3.2, judging whether the internal standard is detected in the spectrum, and if yes, the result is reliable; if not, the result is unreliable, then go to step S31 to acquire the spectrum again.

It can be understood that if the internal standard is detected in the samples, the target ingested substance and its metabolite components are not detected, the negative result is reliable, and the ingestion times by the suspect is zero. If no internal standard is detected in the sample, the negative result is unreliable, and the process returns to step S31 to acquire spectrum again.

Generally speaking, the characteristic ion peaks of drugs, stimulants or psychotropic substances are generally below 1000. Therefore, all known types of drugs, stimulants or psychotropic substances can be obtained by scanning the characteristic ion peaks of drugs, stimulants or psychotropic substances within a certain range. Therefore, as a further improvement, the step of acquiring spectrum comprises:

S33, scanning ions with charge mass ratio of 0 to 2000 to form a mass spectrum.

In addition, the parameters of the matrix assisted laser ionization analysis time-of-flight mass spectrometer also have a great impact on the detection results. Preferably, the parameters of the matrix assisted laser ionization analysis time-of-flight mass spectrometer are: laser wavelength: 308, 337 nm or 405 nm, etc.; laser power: 0.5 to 5 uJ; target high pressure: 10000 to 15000V; pulse high pressure: 1000 to 2000V; detector high pressure: 1500 to 2000V; lens high voltage: 500 to 2000V. In this embodiment, the parameters of the matrix assisted laser ionization analysis time-of-flight mass spectrometer are: laser wavelength: 337 nm; laser power: 1.9 uJ; target high voltage: 13000V; pulse high voltage: 1500V; detector high voltage: 1600V; lens high voltage: 1000V.

As a further improvement, after step S3, the process further comprises:

S4, counting the number of times of detected target ingested substance and its metabolites as the ingestion times.

Please refer to Table 1 below. Table 1 shows the qualitative characteristic ion peaks of common drugs, metabolites and internal standards. According to whether the mass spectrum characteristic ion peaks of drugs exist in the mass spectrum, it can be used as the basis for drug use.

Table 1 shows the qualitative characteristic ion peaks of common drugs, metabolites and internal standards

| Drugs and metabolites | characteristic ion peaks/(m/z) |
|---|---|
| O$^6$-Monoacetylmorphine | 328; 211; 165 |
| Morphine | 286; 201; 165 |
| Codeine | 300; 199; 165 |
| MAMP | 150; 119; 91 |
| AMP | 136; 119; 91 |
| MDMA | 194; 163; 105 |
| MDA | 180; 163; 135 |
| MDEA | 208; 163; 105 |
| Ketamine | 238; 179; 125 |
| Norketamine | 224; 207; 125 |
| Cocaine | 304; 182; 150 |
| Benzoylecgonine | 290; 168; 105 |
| D9-Tetrahydrocannabinol | 315; 259; 193 |
| Cannabidiol | 315; 259; 193 |
| Cannabinol | 311; 293; 223 |
| Methoxyphenamine (internal standard) | 180; 149; 121 |

Figure 3:
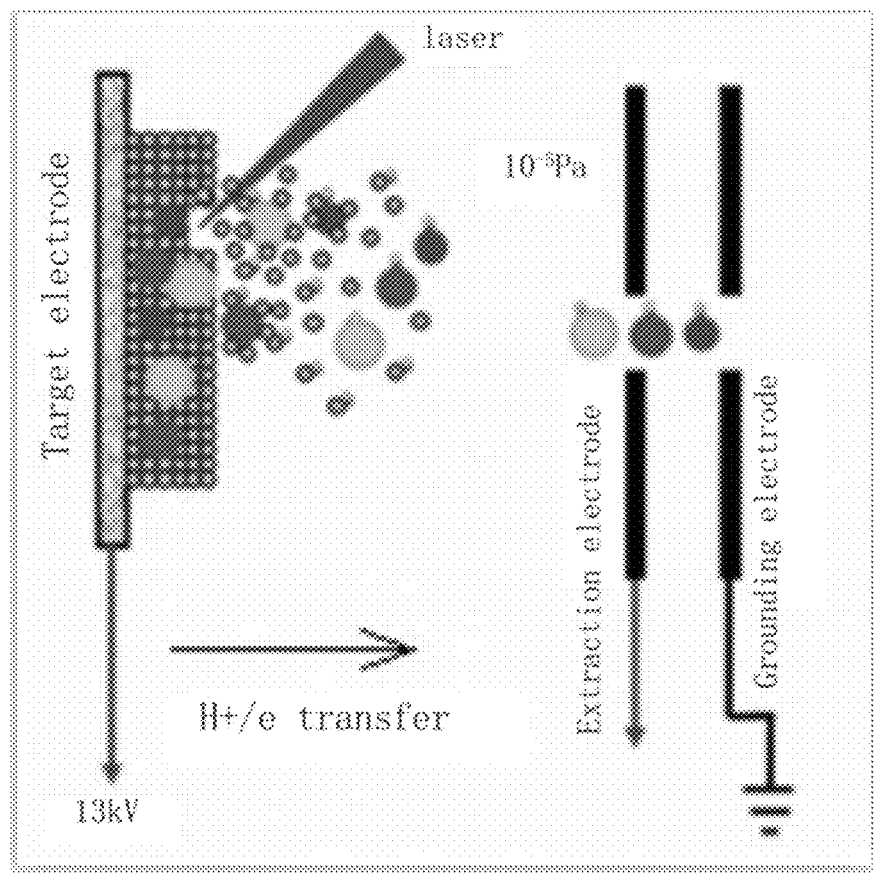
FIG. 3 is a flow chart of the new method for detecting the ingestion times of human ingested substances provided by another embodiment of the disclosure.

Referring to FIG. 3, the embodiment of the disclosure further provides a new method for detecting the ingestion times of human ingested substances, comprising the following steps:

S1, obtaining hair samples or nail samples, wherein the hair samples are obtained by cutting the hair close to the scalp, and the nail samples are obtained by scraping a continuous layer from the root of the nail to the front edge of the nail;

S5, sampling the hair samples or nail samples per unit length, and judging whether the target ingested substance and its metabolites are present in each sample;

S6, counting times of detected target ingested substance and its metabolites as the ingestion times.

In step S5, the metabolites of the target ingested substance, especially drugs, will enter the human hair through daily metabolism. Therefore, the hair samples or nail samples can be sampled per unit length to obtain the ingestion times of the ingested personnel or drug users. Of course, the method to determine whether there is a target ingested substance and its metabolites in each sample is not limited to the matrix assisted laser ionization analysis time-of-flight mass spectrometer provided in this case, other detection methods is also sufficient, such as Raman spectrum.

Embodiment 1

Figure 4:
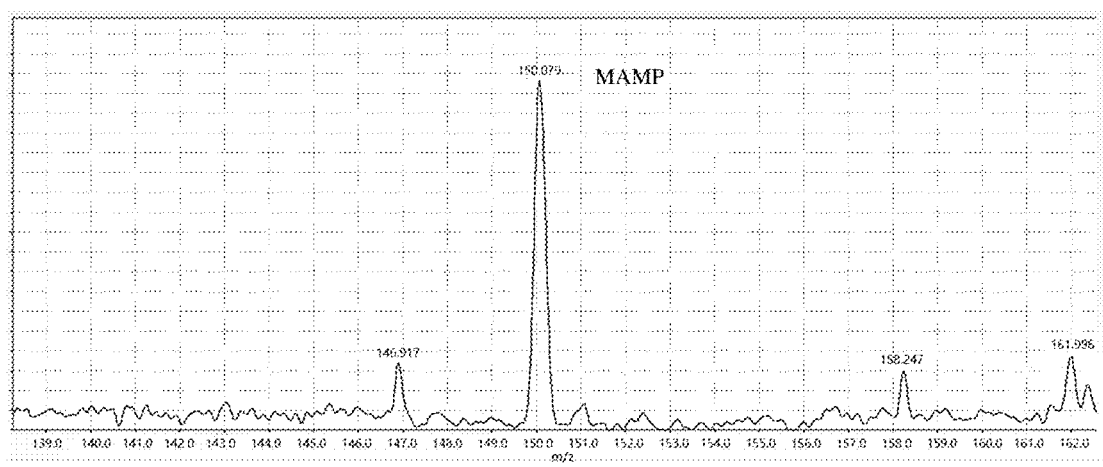
FIG. 4 is a mass spectrum of the hair detected according to embodiment 1.

Please refer to FIG. 4, which is the mass spectrum of the hair detected in embodiment 1, from which it can be seen that the hair has the mass spectrum characteristic ion peak of MAMP.

Embodiment 2

Figure 5:
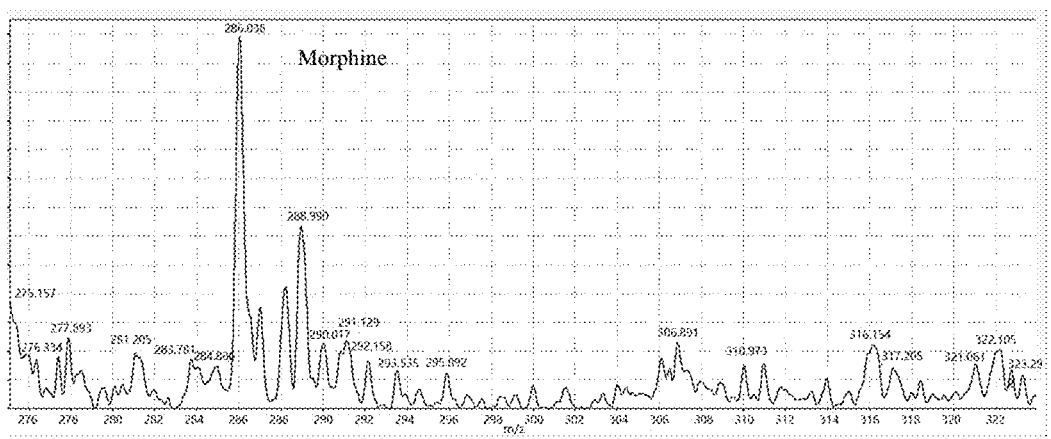
FIG. 5 is a mass spectrum of the hair detected according to embodiment 2.

Please refer to FIG. 5, which is the mass spectrum of the hair detected in embodiment 2. It can be seen that the hair has the mass spectrum characteristic ion peak of morphine.

Embodiment 3

Figure 6:
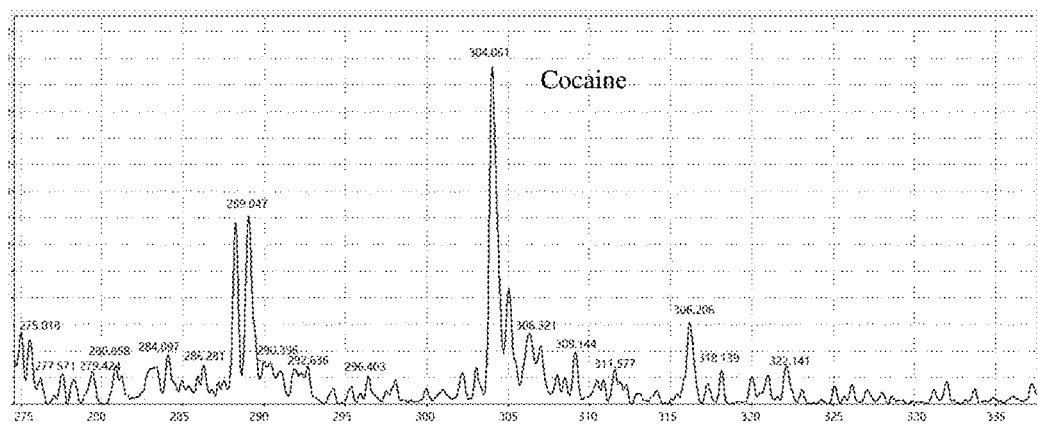
FIG. 6 is a mass spectrum of the hair detected according to embodiment 3.

Please refer to FIG. 6, which is the mass spectrum of the hair detected in Embodiment 3, from which it can be seen that the hair has the mass spectrum characteristic ion peak of cocaine.

The above-described embodiments are intended to illustrate rather than limit the disclosure. Variations may be made to the embodiments without departing from the spirit of the disclosure as claimed. The above-described embodiments illustrate the scope of the disclosure but do not restrict the scope of the disclosure.

What is claimed is:

1. A new method for detecting human ingested substance, comprising the following steps:
   S1, obtaining biological test samples;
   S2, adding matrix solution to the biological test samples, fixing the biological test samples added with matrix solution on a target plate; a matrix in the matrix solution is one or more of 3,5-dimethoxy-4-hydroxycinnamic acid, trihydroxyacetophenone, 3-hydroxypyridylic acid, trihydroxyacetophenone, trans-3-indoleacrylic acid, and desanthrol;
   S3, acquiring a spectrum of biological test samples added with matrix solution with matrix assisted laser ionization analysis time-of-flight mass spectrometer, and taking whether a mass spectrum of a target ingested substance and its metabolites have a characteristic ion peak of mass spectrum as a basis of whether the target ingested substance is ingested;
   the matrix solution further comprises an internal standard; and in step S3, the step of acquiring a spectrum of biological test samples added with matrix solution with matrix assisted laser ionization analysis time-of-flight mass spectrometer comprises:
   S3.1, preliminarily acquiring the spectrum of the hair samples or nail samples added with matrix solution with matrix assisted laser ionization analysis time-of-flight mass spectrometer;
   S3.2, judging whether the internal standard is detected in the mass spectrum, yes, the result is reliable; no, the result is unreliable, then go to step S3.1 to collect the spectrum again;
   the internal standard is methoxyphenamine;
   parameters of the matrix assisted laser ionization analysis time-of-flight mass spectrometer are: laser wavelength: 308, 337 nm or 405 nm; laser power: 0.5~5 uJ; target high pressure: 10000~15000V; pulse high pressure: 1000~2000V; detector high pressure: 1500~2000 V; lens high voltage: 500~2000 v.

2. The new method for detecting human ingested substance according to claim 1, wherein the biological test samples are hair samples or nail samples, in step S1, after obtaining the biological test samples, further comprising:
   S1.1 washing the hair samples or the nail samples to remove contaminants.

3. The new method for detecting human ingested substance according to claim 2, wherein in step S2, the step of fixing the biological test samples added with matrix solution on a target plate comprises:
   S2.1, fixing the hair samples or nail samples on a target plate;
   S2.2, adding the matrix solution to the hair samples or the nail samples, and volatilizing a solvent.

4. The new method for detecting human ingested substance according to claim 1, wherein in step S3.1, the step of acquiring the spectrum of the hair samples or nail samples added with matrix solution with matrix assisted laser ionization analysis time-of-flight mass spectrometer comprises:
   S3.1.1 acquiring the spectrum of the hair samples or nail samples added with matrix solution with matrix assisted laser ionization analysis time-of-flight mass spectrometer at interval of unit length.

5. The new method for detecting human ingested substance according to claim 4, wherein the unit length is 0.2-0.4 mm.

6. The new method for detecting human ingested substance according to claim 1, wherein the step of acquiring a spectrum of biological test samples added with matrix solution with matrix assisted laser ionization analysis time-of-flight mass spectrometer comprises:
   S3.3, scanning ions with charge mass ratio of 0~2000 to form mass spectrum.

7. The new method for detecting human ingested substance according to claim 1, wherein the target ingested substance is drugs or stimulants.

* * * * *